United States Patent
Djeu

(10) Patent No.: US 8,592,768 B1
(45) Date of Patent: Nov. 26, 2013

(54) ANGULARLY PARTITIONED EVANESCENT WAVE ABSORPTION SENSOR

(75) Inventor: Nicholas Djeu, Tampa, FL (US)

(73) Assignee: University of South Florida, Tampa, FL (US)

( * ) Notice: Subject to any disclaimer, the term of this patent is extended or adjusted under 35 U.S.C. 154(b) by 858 days.

(21) Appl. No.: 12/755,093

(22) Filed: Apr. 6, 2010

Related U.S. Application Data

(60) Provisional application No. 61/166,961, filed on Apr. 6, 2009.

(51) Int. Cl.
*G01J 5/02* (2006.01)
*G02B 6/00* (2006.01)
*G02B 6/42* (2006.01)
*G02B 6/32* (2006.01)
*G01N 21/47* (2006.01)

(52) U.S. Cl.
USPC ............ 250/339.12; 385/12; 385/30; 385/33; 385/34; 356/446

(58) Field of Classification Search
USPC ............... 250/339.12; 385/12, 30, 33, 34; 356/446
See application file for complete search history.

(56) References Cited

U.S. PATENT DOCUMENTS

| | | | | |
|---|---|---|---|---|
| 3,673,933 | A | * | 7/1972 | Hamann ..................... 396/332 |
| 4,566,765 | A | * | 1/1986 | Miyauchi et al. ............. 359/618 |
| 5,399,866 | A | * | 3/1995 | Feldman et al. ........... 250/458.1 |
| 2003/0155527 | A1 | * | 8/2003 | Natori ........................ 250/458.1 |

* cited by examiner

*Primary Examiner* — David Porta
*Assistant Examiner* — Mindy Vu
(74) *Attorney, Agent, or Firm* — Andriy Lytvyn; Jeremy Spier; Smith & Hopen, P.A.

(57) ABSTRACT

A fiber optic evanescent absorption sensor. This invention makes use of two sources and one detection system, or one source and two detection systems, or two of each to determine a large range of absorbance with high accuracy for a fixed interaction length.

10 Claims, 2 Drawing Sheets

ANGULARLY PARTITIONED EVANESCENT WAVE ABSORPTION SENSOR

CROSS REFERENCE TO RELATED APPLICATION

This application claims priority to currently U.S. Provisional Patent Application No. 61/166,961, entitled "ANGULARLY POSITIONED EVANESCENT WAVE ABSORPTION SENSOR", filed on Apr. 6, 2009, the contents of which are hereby incorporated by reference.

BACKGROUND OF THE INVENTION

1. Field of the Invention

This invention relates to the field of spectroscopy. More specifically, this invention relates to a fiber optic evanescent absorption sensor.

2. Description of the Prior Art

In conventional absorption spectroscopy, the accurate determination of the absorbance on a given band in the absorbing medium requires an optimum path length. Thus, a more strongly absorbing band requires a shorter path than a weaker one. Similarly, an absorption measuring apparatus with a fixed path length cannot be optimal for the measurement of absorption on a number of bands with widely different absorption coefficients.

A conventional fiber optic evanescent wave absorption sensor uses one source and one detection system and is optimized for measuring absorbance that varies in magnitude by a factor of approximately 30. On the other hand, for example, the absorbance in the mid-IR is typically 100 times or more larger than that in the near-IR, and therefore the conventional evanescent wave absorption sensor cannot be configured to be optimal for both regions.

What is needed is a device and method that permits a larger range of absorbance to be determined with high accuracy for a fixed interaction length.

However, in view of the prior art considered as a whole at the time the present invention was made, it was not obvious to those of ordinary skill in the art how the limitations of the art could be overcome.

SUMMARY OF INVENTION

An evanescent wave absorption sensor can be made optimal for measuring a wide range of absorbance if large angle rays are used for the weaker bands and small-angle rays are used for the stronger bands. This invention makes use of two sources and one detection system or one source and two detection systems, or two of each to accomplish the same. In the scheme where two separate light sources are used, one provides signal in the wavelength region of the weak absorption band ($\lambda_w$) and the other for the strong absorption band ($\lambda_s$). Light at $\lambda_w$ starts out as a wide beam, and is turned into an annular beam by a mirror with an aperture. An additional disk-shaped beam stop may be used to produce a beam with a larger inside diameter. Light at $\lambda_s$ is in the form of a narrow beam, and after passing through the aperture in the mirror, is focused together with light at $\lambda_w$ by lens $L_1$ into the evanescent wave fiber in the probe. The latter has no cladding in the region of interaction with the sample. The output from the fiber is focused by the lens $L_2$ into a detection system consisting of a spectrometer and associated data processor. Thus, it can cover both near and mid-IR regions and thus can be used to measure a wide range of absorbance.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention The evanescent wave absorption sensor is based on the principle that any propagating ray in the core of an optical fiber penetrates slightly into the cladding, and therefore will be attenuated if the cladding is absorbing. If the cladding is replaced by a sample chemical, the absorption characteristics of the sample can be probed. The relationship between the evanescent wave absorption coefficient $\gamma$ and the bulk absorption coefficient $\alpha$ is given approximately by:

$$\gamma = \frac{\lambda}{2\pi\rho n_2} \frac{\theta^2}{\theta_c^2 \sqrt{\theta_c^2 - \theta^2}} \alpha$$

Where $\lambda$ is the wavelength of the light, $\rho$ the radius of the fiber, $n_2$ the refractive index of the sample, $\theta$ the angle between the ray and the fiber axis, and $\theta_c$ the complementary critical angle of the fiber/sample interface. The evanescent wave absorption coefficient increases rapidly with $\theta$ both because of the $\theta^2$ dependence in the numerator and the $$\sqrt{\theta_c^2 - \theta^2}$$

dependence in the denominator. As an example, for $\theta_c$=0.6 radians, $\gamma$ increases by a factor of about 50 when $\theta$ increases from 0.1 rad to 0.5 rad. Thus, an evanescent wave absorption probe can be made optimal for measuring a wide range of absorbance if large-angle rays are used for the weaker bands and small-angle rays for the stronger ones.

Figure 1:
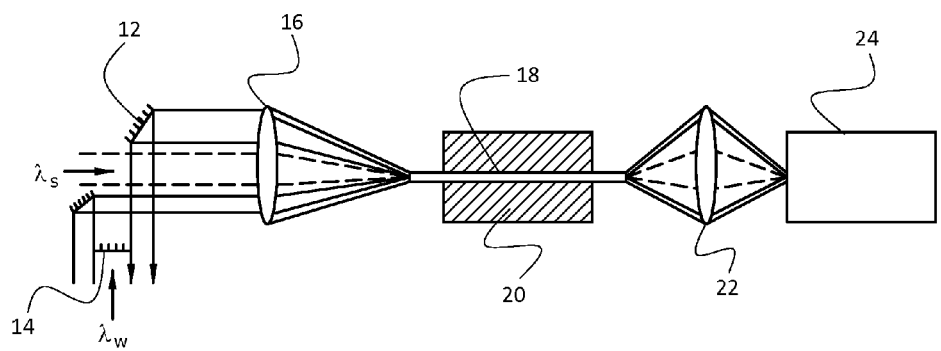
FIG. 1 is a schematic for implementing the inventive method.

As shown in FIG. 1, two separate light sources are used, one to provide signal in the wavelength region of the weak absorption band ($\lambda_w$) and the other for the strong absorption band ($\lambda_s$). Light at $\lambda_w$ starts out as a wide beam, and is turned into an annular beam by a mirror 12 with an aperture. An additional disk-shaped beam stop 14 may be used to produce a beam with a larger inside diameter. Light at $\lambda_s$ is in the form of a narrow beam, and after passing through the aperture in the beam combining mirror 12 is focused together with light at $\lambda_w$ by first lens 16 into an evanescent wave fiber 18 in the probe. The latter has no cladding in the region of interaction with a sample 20. The output from fiber 18 is focused by second lens 22 into a detection system 24 comprising a spectrometer and associated data processor.

Figure 2:
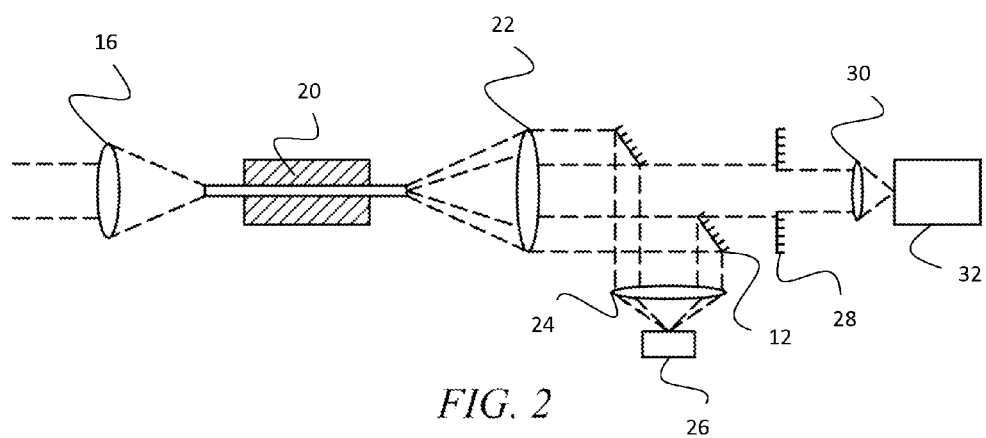
FIG. 2 is a schematic of an alternate means for implementing the inventive method.

Alternatively, as shown in FIG. 2, a single source and two separate detection systems are used. Light is focused by first lens 16 into fiber 18 and collimated by second lens 22 after exiting fiber 18. The large angle rays are separated from the small angle ones by mirror 12 with an aperture. The former are focused by a fourth lens 24 onto a first detection system 26 for the analysis of the weak absorption bands, while the latter is focused by a third lens 30 onto a second detection system 32 for the analysis of the strong absorption bands. An additional iris 30 may be used to further reduce the angular range for measuring absorption on the strong bands. Since some mode mixing in the fiber is inevitable, both schemes may be implemented together to maximize angular separation, and achieve the largest range of optimal sensing.

One important area of application for this concept is infrared (IR) spectroscopy. At present, the options are divided into near-IR (below 2.5 µm and for weak bands), and mid-IR (above 2.5 µm and for strong bands) types. The present invention opens the way to the instrumentation of a spectroscopic system which can cover both the near-IR and mid-IR regions. A sapphire fiber, for example, which has good transmission to 4 µm, can be used as the evanescent wave probe in such a system.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

What is claimed is:

1. A fiber optic evanescent absorption sensor, comprising:
a first light source, said first light source provides a signal in a wavelength region of a weak absorption band;
a second light source, said second light source provides a signal in a wavelength region of a strong absorption band;
a mirror with an aperture;
a sample;
an evanescent wave fiber within said sample having no cladding in a region of interaction with said sample;
a first lens;
a second lens;
a detection system;
whereby light from said first light source originates as a wide beam and is converted into an annular beam by said mirror with said aperture;
whereby light from said second light source is a narrow beam and is passed through said mirror with said aperture and is focused together with said light from said first light source by said first lens and directed into said evanescent wave fiber;
whereby said light from said first and second light sources experiences absorption within said evanescent wave fiber in said region of interaction with said sample; and
whereby an output from said evanescent fiber is focused by said second lens into said detection system, said detection system adapted to analyze absorption characteristics of said sample.

2. A fiber optic evanescent absorption sensor of claim 1, further comprising:
a disk-shaped beam stop to produce a beam with a larger inside diameter for said first light source.

3. A fiber optic evanescent absorption sensor of claim 1, further comprising:
said detection system being a spectrometer and a data processor.

4. A fiber optic evanescent absorption sensor, comprising:
a light source;
a first lens;
a second lens;
a third lens;
a fourth lens;
a mirror with an aperture;
a sample;
an evanescent wave fiber within said sample having no cladding in a region of interaction with said sample;
a first detection system;
a second detection system;
whereby light from said light source is focused by said first lens into said evanescent wave fiber within said sample;
whereby said light from said light source experiences absorption within said evanescent wave fiber in said region of interaction with said sample;
whereby an output from said evanescent fiber is collimated by said second lens; and
whereby large angle rays are separated from small angle rays by said mirror with said aperture, said large angle rays are focused by said fourth lens into said first detection system for analysis of weak absorption bands, said small angle rays are focused by said third lens into said second detection system for analysis of strong absorption bands.

5. A fiber optic evanescent absorption sensor of claim 4, further comprising:
an iris to further reduce the angular range for measuring absorption on said strong absorption bands.

6. A fiber optic evanescent absorption sensor of claim 4, further comprising:
said first detection system and said second detection system comprising a spectrometer and a data processor.

7. A fiber optic evanescent absorption sensor, comprising:
a first light source, said first light source provides a signal in a wavelength region of a weak absorption band;
a second light source, said second light source provides a signal in a wavelength region of a strong absorption band;
a first mirror with a first aperture;
a second mirror with a second aperture;
a sample;
an evanescent wave fiber within said sample having no cladding in a region of interaction with said sample;
a first lens;
a second lens;
a third lens;
a fourth lens;
a first detection system;
a second detection system;
whereby light from said first light source originates as a wide beam and is converted into an annular beam by said first mirror with said first aperture;
whereby light from said second light source is a narrow beam and is passed through said first mirror with said first aperture and is focused together with light from said second light source by said first lens and directed into said evanescent wave fiber;
whereby said light from said first and second light sources experiences absorption within said evanescent wave fiber in said region of interaction with said sample;
whereby an output from said evanescent fiber is collimated by said second lens; and
whereby large angle rays are separated from small angle rays by said second mirror with said second aperture, said large angle rays are focused by said fourth lens into said first detection system for analysis of weak absorption bands, said small angle rays are focused by said third lens into said second detection system for analysis of strong absorption bands.

8. A fiber optic evanescent absorption sensor of claim 7, further comprising:
   a disk-shaped beam stop to produce an annular beam of said first light source with a larger inside diameter.

9. A fiber optic evanescent absorption sensor of claim 7, further comprising:
   an iris to further reduce the angular range for measuring absorption on said strong absorption bands.

10. A fiber optic evanescent absorption sensor of claim 7, further comprising:
    said first detection system and said second detection system comprising a spectrometer and a data processor.

\* \* \* \* \*